US00PP22436P2

(12) United States Plant Patent
Bergman

(10) Patent No.: US PP22,436 P2
(45) Date of Patent: Jan. 3, 2012

(54) ***CHRYSANTHEMUM* PLANT NAMED 'SYNGOLD EMPORIA'**

(50) Latin Name: *Chrysanthemum×morifolium*
Varietal Denomination: Syngold Emporia

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/802,380

(22) Filed: Jun. 4, 2010

(51) Int. Cl.
*A01H 5/00* (2006.01)

(52) U.S. Cl. ..... Plt./295

(58) Field of Classification Search ..... Plt./295, Plt./296, 286
See application file for complete search history.

(56) References Cited

OTHER PUBLICATIONS

Dana et al. Chrysanthemums. Purdue University Cooperative Extension Service, RR 9/96 (1996) HO-77, 2 pages.*

* cited by examiner

*Primary Examiner* — June Hwu
(74) *Attorney, Agent, or Firm* — S. Matthew Edwards

(57) ABSTRACT

A new *Chrysanthemum* plant named 'Syngold Emporia' particularly distinguished by the bright yellow ray floret color with green discs at the early age, daisy-type flowers with spoon-shaped ray florets, strong stems, good shelf-life, and about an 8 week flowering response time.

1 Drawing Sheet

Latin name of the genus and species of the plant claimed: *Chrysanthemum×morifolium.*

Varietal denomination: 'Syngold Emporia'.

BACKGROUND OF THE NEW PLANT

The present invention comprises a new *Chrysanthemum,* botanically known as *Chrysanthemum×morifolium,* and hereinafter referred to by the variety name 'Syngold Emporia'.

'Syngold Emporia' is a product of a planned breeding program. The new cultivar has bright yellow ray floret color with green discs at the early age, daisy-type flowers with spoon-shaped ray florets, strong stems, good shelf-life; and about an 8 week flowering response time.

'Syngold Emporia' originated from a hybridization made in February 2005 in a controlled breeding environment in Salinas, Calif. The female parent was the unpatented proprietary plant designated 'YB-F0125', with grainy orange flower color and ligulate ray florets.

The male parent of 'Syngold Emporia' was an unpatented proprietary plant designated as 'YB-6604' with yellow flower color, ligulate ray florets, and is a heavy pollen producer. The seed of this cross was sown in October 2005.

'Syngold Emporia' was selected as one flowering plant within the progeny of the stated cross in February 2006 in a controlled environment in Fort Myers, Fla.

The first act of asexual reproduction of 'Syngold Emporia' was accomplished when vegetative cuttings were propagated from the initial selection in May 2006, in a controlled environment in Fort Myers, Fla.

BRIEF SUMMARY OF INVENTION

Horticultural examination of plants grown from cuttings of the plant initiated in May 2006, and continuing thereafter, has demonstrated that the combination of characteristics as herein disclosed for 'Syngold Emporia' are firmly fixed and are retained through successive generations of asexual reproduction.

'Syngold Emporia' has not been observed under all possible environmental conditions. The phenotype may vary significantly with variations in environment such as temperature, light intensity and day length.

A Plant Breeder's Right for this cultivar was applied for in Canada on Oct. 30, 2009 (#09-6764). 'Syngold Emporia' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Syngold Emporia' with colors being as true as possible with an illustration of this type. The photographic drawing shows four flowering plants of the new variety growing in a 6 inch pot, and a close-up of the flowers.

DETAILED BOTANICAL DESCRIPTION

The plant descriptions, measurements and aforementioned photographs were taken in Gilroy, Calif. in April 2010 under natural light. These plants were started and grown in Nipomo, Calif. and were shipped to Gilroy in April. Plants were grown under conditions which approximate those generally used in commercial potted chrysanthemum production. These plants used in the photograph and descriptions were about 10 weeks old.

Color references are made to The Royal Horticultural Society Colour Chart (R.H.S.) 2001.

TABLE 1

DIFFERENCES BETWEEN THE NEW VARIETY 'SYNGOLD EMPORIA' AND A SIMILAR VARIETY

| | 'Syngold Emporia' | 'Yochesapeake' (U.S. Plant Pat. No. 12,535) |
|---|---|---|
| Ray floret width: | Longer | Shorter |
| Disc floret quantity: | About 150-200 | About 230-250 |
| Foliage length: | Longer | Shorter |

Plant:
- *Form, growth and habit.*—Herbaceous pot-type. Stems upright and outwardly spreading, strong stems, good shelf life, suitable for production using center budded or no bud removal.
- *Plant height.*—17-20 cm.
- *Plant height (inflorescence included).*—25-28 cm.
- *Plant width.*—37-40 cm.

Roots:
- *Number of days to initiate roots.*—4 days at about 22 degrees C.
- *Number of days to produce a rooted cutting.*—10 days at 22 degrees C.
- *Type.*—Fine, fibrous, free branching.
- *Color.*—RHS N155B but whiter.

Foliage:
- *Arrangement.*—Alternate.
- *Immature, leaf color, upper surface.*—Between RHS 147A and RHS 147B.
- *Lower surface.*—RHS 137B.
- *Mature, leaf color, upper surface.*—Between RHS 147A and RHS 146A.
- *Lower surface.*—Closest to RHS 147B but more green.
- *Length.*—7.5-10.4 cm.
- *Width.*—5.0-5.7 cm.
- *Shape.*—Ovate.
- *Base shape.*—Attenuate.
- *Apex shape.*—Mucronulate.
- *Margin.*—Palmately lobed, slightly crenate.
- *Texture, upper surface.*—Bi-fid T-shaped hairs.
- *Lower surface.*—Bi-fid T-shaped hairs.
- *Color of veins, upper surface.*—RHS 146C.
- *Color of veins, lower surface.*—RHS 146B.
- *Petiole color.*—RHS 146C.
- *Length.*—2.0-2.7 cm.
- *Diameter.*—0.35 cm.
- *Texture.*—Bi-fid T-shaped hairs.

Stem:
- *Quantity of main branches per plant.*—4-5.
- *Color of stem.*—RHS 146B.
- *Length of stem.*—17-20 cm.
- *Diameter.*—0.4 cm.
- *Length of internodes.*—1.5-3.5 cm.
- *Texture.*—Bi-fid T-shaped hairs.
- *Color of peduncle.*—RHS 146C.
- *Length of peduncle.*—5.0-6.4 cm.
- *Peduncle diameter.*—0.2 cm.
- *Texture.*—Bi-fid T-shaped hairs.

Inflorescence:
- *Type.*—Composite type, solitary inflorescences (daisy-type) borne terminally above foliage, ray florets arranged acropetally on a capitulum.
- *Quantity of short days to flowering (response time).*—52-56 days.
- *Quantity of inflorescences per plant.*—About 25.
- *Lastingness of individual blooms on the plant.*—About 14 days.
- *Fragrance.*—Slight.

Bud (just before opening/showing color):
- *Color.*—RHS 3B with RHS 4C basally.
- *Length.*—0.5-1.0 cm.
- *Width.*—0.5-0.7 cm.
- *Shape.*—Oblate.

Immature inflorescence:
- *Diameter.*—6.0-7.0 cm.
- *Color of ray florets, upper surface.*—RHS 9A with a hint of RHS 14B basally.
- *Lower surface.*—RHS 7B.

Mature inflorescence:
- *Diameter.*—9.0 cm.
- *Depth.*—2.5-3.0 cm, some a slightly cupped.
- *Total diameter of 'disc'.*—1.7 cm.
- *Receptacle height.*—0.7 cm.
- *Receptacle diameter.*—0.6-0.7 cm.

Ray florets:
- *Average quantity of florets.*—35 in 2-3 whorls.
- *Color of florets, upper surface.*—RHS 9A.
- *Lower surface.*—RHS 8A.
- *Length.*—4.1-4.5 cm.
- *Width.*—0.7-0.9 cm.
- *Shape.*—Spoon-shaped; tube is about 1.2-2.1 cm in length.
- *Apex shape.*—Acute to praemorse.
- *Margin.*—Entire.
- *Texture, upper surface.*—Papillose.
- *Lower surface.*—Papillose.
- *Spoon length.*—1.8-2.4 cm.

Disc florets:
- *Average quantity of florets.*—150-200.
- *Color of florets.*—RHS 1D with overlay of RHS 8C to RHS 8D at apex end, and RHS 9B at the very apex.
- *Length.*—0.6-0.7 cm.
- *Width.*—0.1-0.15 cm.
- *Shape.*—Tubular, elongated.
- *Apex shape.*—Acute, 5 pointed.

Phyllaries:
- *Quantity.*—26-30.
- *Color, upper surface.*—RHS 137B but appears lighter being heavily covered with hairs.
- *Lower surface.*—RHS 137B.
- *Length.*—0.4-0.6 cm.
- *Width.*—0.15-0.2 cm.
- *Shape.*—Lanceolate.
- *Apex shape.*—Acute.
- *Based.*—Fused.
- *Margins.*—Entire, papery.
- *Texture, upper surface.*—Glossy, glabrous.
- *Lower surface.*—Bi-fid T-shaped hairs.

Reproductive organs:
- *Found on both florets.*—Pistil: 1. Length: 0.7 cm. Style color: RHS 9B. Style length: 0.6 cm. Stigma color: RHS 9B.
- *Stigma shape.*—Bi-parted.
- *Ovary color.*—Not observed.
- *Found on only disc floret.*—Stamens: 1. Color of filaments: RHS 155C but more green. Length filaments: 0.4-0.5 cm. Anther color: About RHS 15B. Anther length: 0.2 cm. Anther shape: Oblong. Color of pollen: RHS 15A. Pollen amount: Excellent. Fertility/seed set: Has not been observed on this hybrid.

Disease/pest resistance: Disease/pest resistance has not been observed on this hybrid.

What is claimed is:

1. A new and distinct variety of *Chrysanthemum* plant named 'Syngold Emporia' substantially as illustrated and described herein.

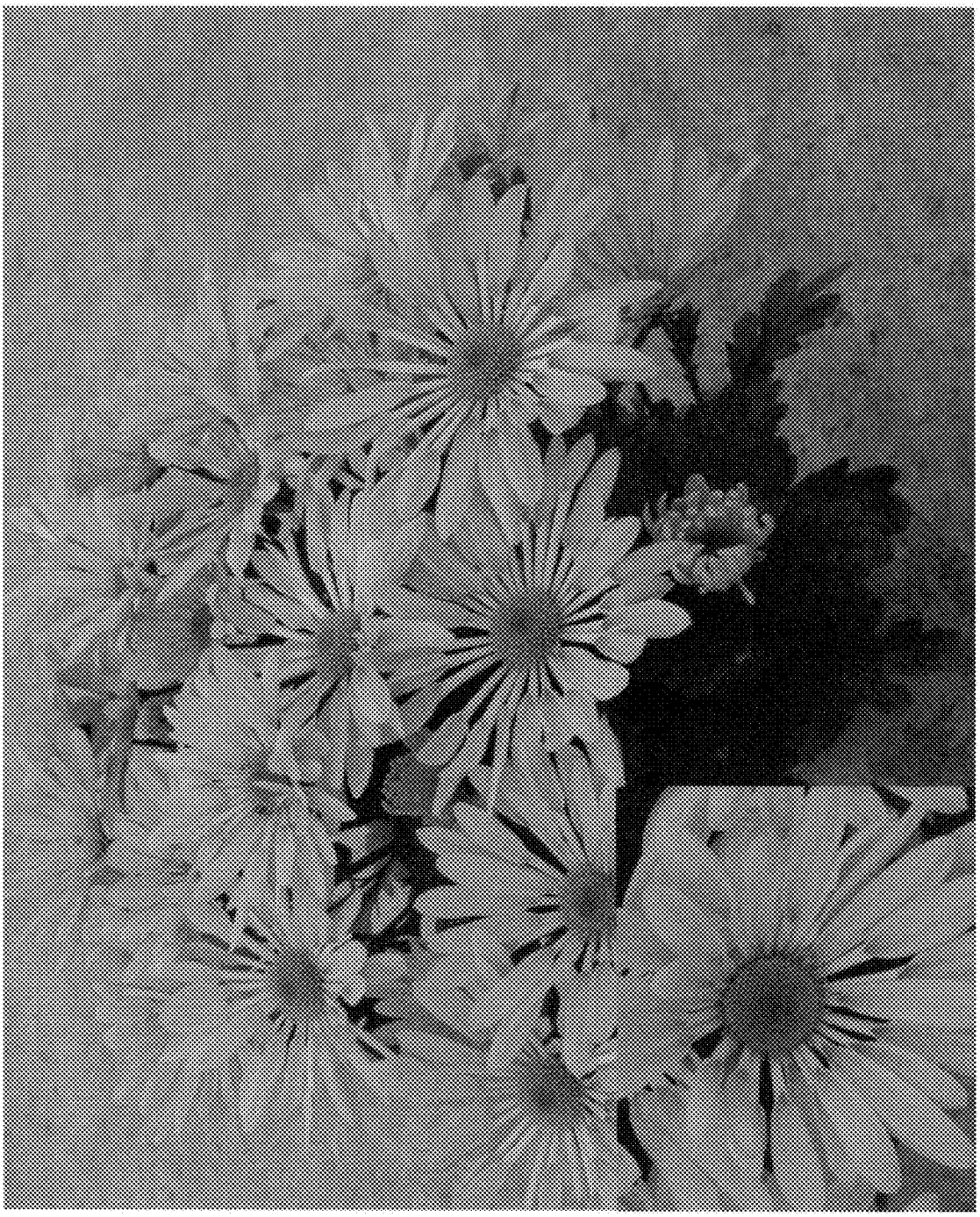

* * * * *